United States Patent
Sakuma et al.

(10) Patent No.: US 10,501,564 B2
(45) Date of Patent: Dec. 10, 2019

(54) POLYMER COMPOUND WHICH HAS MEMBRANE-PERMEABLE PEPTIDE IN SIDE CHAIN

(71) Applicants: JOSHO GAKUEN EDUCATIONAL FOUNDATION, Osaka (JP); ADEKA CORPORATION, Tokyo (JP)

(72) Inventors: Shinji Sakuma, Osaka (JP); Kohta Mohri, Osaka (JP); Ken-ichiro Hiwatari, Tokyo (JP); Kyohei Ochiai, Tokyo (JP)

(73) Assignees: JOSHO GAKUEN EDUCATIONAL FOUNDATION, Osaka (JP); ADEKA CORPORATION, Tokyo (JP)

(*) Notice: Subject to any disclaimer, the term of this patent is extended or adjusted under 35 U.S.C. 154(b) by 0 days.

(21) Appl. No.: 15/547,840

(22) PCT Filed: Feb. 23, 2016

(86) PCT No.: PCT/JP2016/055174
§ 371 (c)(1),
(2) Date: Aug. 1, 2017

(87) PCT Pub. No.: WO2016/136708
PCT Pub. Date: Sep. 1, 2016

(65) Prior Publication Data
US 2018/0016366 A1    Jan. 18, 2018

(30) Foreign Application Priority Data
Feb. 27, 2015  (JP) ................. 2015-038433

(51) Int. Cl.
| | | |
|---|---|---|
| *A61K 38/08* | (2019.01) | |
| *C08F 8/30* | (2006.01) | |
| *C07K 2/00* | (2006.01) | |
| *C08G 81/00* | (2006.01) | |
| *C08F 220/06* | (2006.01) | |
| *C08F 220/56* | (2006.01) | |
| *A61K 47/32* | (2006.01) | |
| *C07K 5/062* | (2006.01) | |
| *C08F 226/02* | (2006.01) | |

(52) U.S. Cl.
CPC ............ *C08F 8/30* (2013.01); *A61K 47/32* (2013.01); *C07K 2/00* (2013.01); *C07K 5/06026* (2013.01); *C08F 220/06* (2013.01); *C08F 220/56* (2013.01); *C08F 226/02* (2013.01); *C08G 81/00* (2013.01)

(58) Field of Classification Search
None
See application file for complete search history.

(56) References Cited

U.S. PATENT DOCUMENTS

| 2003/0229202 A1 | 12/2003 | Guo et al. |
| 2010/0113559 A1 | 5/2010 | Park et al. |
| 2011/0020229 A1* | 1/2011 | Waugh ................. A61K 49/128 424/9.1 |

FOREIGN PATENT DOCUMENTS

| JP | 2005-052083 | 3/2005 |
| JP | 2010-100781 | 5/2010 |
| JP | 2010100781 A * | 5/2010 |
| JP | 2011-229495 | 11/2011 |

OTHER PUBLICATIONS

Blum, J. Am. Chem. Soc. 2014, 136, 15422-15437 (Year: 2014).*
Ruttekolk, Bioconjugate Chem. 2008, 19, 2081-2087 (Year: 2008).*
Cohen, Bioconjugate Chem. 2008, 19, 876-831 (Year: 2008)*
Sakuma, Journal of Controlled Release 148 (2010) 187-196 (Year: 2010).*
International Search Report, PCT/JP2016/055174, dated Apr. 12, 2016.
Liu J et al., A Facile strategy toward Conjugated Polyelectrolyte with Oligopeptide as Pendants for Biological Applications, ACS Applied Materials & Interfaces, 2013, vol. 5, No. 11, pp. 4511-4515.
Sakuma S et al., Performance of cell-penetrating peptide-linked polymers physically mixed with poorly membrane-permeable molecules on cell membranes, European Journal of Pharmaceutics and Biopharmaceutics, 2012, vol. 81, pp. 64-73.

* cited by examiner

*Primary Examiner* — Satyanarayana R Gudibande
(74) *Attorney, Agent, or Firm* — Young & Thompson

(57) ABSTRACT

A polymer compound has a group represented by Formula (1) or Formula (2) in a side chain.

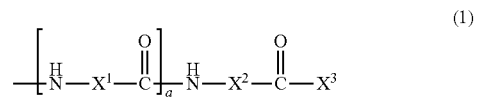

(1)

(In Formula (1), $X^1$ represents a neutral amino acid residue or an ω-aminoalkanoic acid residue, $X^2$ represents a membrane-permeable peptide residue, $X^3$ represents a hydroxyl group, an amino group, an alkoxyl group having 1 to 4 carbon atoms, or a benzyloxy group, and a represents a number of from 1 to 50.)

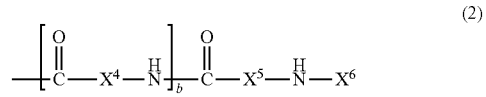

(2)

(In Formula (2), $X^4$ represents a neutral amino acid residue or an ω-aminoalkanoic acid residue, $X^5$ represents a membrane-permeable peptide residue, $X^6$ represents a hydrogen atom, an alkyl group having 1 to 6 carbon atoms, a benzyl group, an acyl group having 1 to 6 carbon atoms, an arylsulfonyl group, or a carboxyl group, and b represents a number of from 1 to 50.).

4 Claims, No Drawings

Specification includes a Sequence Listing.

SEQUENCE LISTING

```
<160> NUMBER OF SEQ ID NOS: 12

<210> SEQ ID NO 1
<211> LENGTH: 13
<212> TYPE: PRT
<213> ORGANISM: Artificial Sequence
<220> FEATURE:
<223> OTHER INFORMATION: Hydrophilic basic peptide

<400> SEQUENCE: 1

Gly Arg Lys Lys Arg Arg Gln Arg Arg Arg Pro Pro Gln
1               5                   10

<210> SEQ ID NO 2
<211> LENGTH: 17
<212> TYPE: PRT
<213> ORGANISM: Artificial Sequence
<220> FEATURE:
<223> OTHER INFORMATION: Hydrophilic basic peptide

<400> SEQUENCE: 2

Thr Arg Gln Ala Arg Arg Asn Arg Arg Arg Arg Trp Arg Glu Arg Gln
1               5                   10                  15

Arg

<210> SEQ ID NO 3
<211> LENGTH: 15
<212> TYPE: PRT
<213> ORGANISM: Artificial Sequence
<220> FEATURE:
<223> OTHER INFORMATION: Hydrophilic basic peptide

<400> SEQUENCE: 3

Arg Arg Arg Arg Asn Arg Thr Arg Arg Asn Arg Arg Arg Val Arg
1               5                   10                  15

<210> SEQ ID NO 4
<211> LENGTH: 13
<212> TYPE: PRT
<213> ORGANISM: Artificial Sequence
<220> FEATURE:
<223> OTHER INFORMATION: Hydrophilic basic peptide

<400> SEQUENCE: 4

Thr Arg Arg Gln Arg Thr Arg Arg Ala Arg Arg Asn Arg
1               5                   10

<210> SEQ ID NO 5
<211> LENGTH: 19
<212> TYPE: PRT
<213> ORGANISM: Artificial Sequence
<220> FEATURE:
<223> OTHER INFORMATION: Hydrophilic basic peptide
```

<400> SEQUENCE: 5

Lys Leu Thr Arg Ala Gln Arg Arg Ala Ala Ala Arg Lys Asn Lys Arg
1               5                   10                  15

Asn Thr Arg

<210> SEQ ID NO 6
<211> LENGTH: 16
<212> TYPE: PRT
<213> ORGANISM: Artificial Sequence
<220> FEATURE:
<223> OTHER INFORMATION: Amphiphilic basic peptide

<400> SEQUENCE: 6

Arg Gln Ile Lys Ile Trp Phe Gln Asn Arg Arg Met Lys Trp Lys Lys
1               5                   10                  15

<210> SEQ ID NO 7
<211> LENGTH: 19
<212> TYPE: PRT
<213> ORGANISM: Artificial Sequence
<220> FEATURE:
<223> OTHER INFORMATION: Amphiphilic basic peptide

<400> SEQUENCE: 7

Lys Met Thr Arg Ala Gln Arg Arg Ala Ala Ala Arg Arg Asn Arg Trp
1               5                   10                  15

Thr Ala Arg

<210> SEQ ID NO 8
<211> LENGTH: 16
<212> TYPE: PRT
<213> ORGANISM: Artificial Sequence
<220> FEATURE:
<223> OTHER INFORMATION: Amphiphilic basic peptide

<400> SEQUENCE: 8

Arg Gln Ile Lys Ile Trp Phe Gln Asn Arg Arg Met Lys Trp Lys Lys
1               5                   10                  15

<210> SEQ ID NO 9
<211> LENGTH: 17
<212> TYPE: PRT
<213> ORGANISM: Artificial Sequence
<220> FEATURE:
<223> OTHER INFORMATION: Amphiphilic basic peptide

<400> SEQUENCE: 9

Asn Ala Lys Thr Arg Arg His Glu Arg Arg Arg Lys Leu Ala Ile Glu
1               5                   10                  15

Arg

<210> SEQ ID NO 10
<211> LENGTH: 34
<212> TYPE: PRT
<213> ORGANISM: Artificial Sequence
<220> FEATURE:
<223> OTHER INFORMATION: Amphiphilic basic peptide

```
<400> SEQUENCE: 10

Asp Ala Ala Thr Ala Thr Arg Gly Arg Ser Ala Ala Ser Arg Pro Thr
1               5                   10                  15

Glu Arg Pro Arg Ala Pro Ala Arg Ser Ala Ser Arg Pro Asp Asp Pro
            20                  25                  30

Val Asp

<210> SEQ ID NO 11
<211> LENGTH: 27
<212> TYPE: PRT
<213> ORGANISM: Artificial Sequence
<220> FEATURE:
<223> OTHER INFORMATION: Hydrophobic basic peptide

<400> SEQUENCE: 11

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 12
<211> LENGTH: 21
<212> TYPE: PRT
<213> ORGANISM: Artificial Sequence
<220> FEATURE:
<223> OTHER INFORMATION: Hydrophobic basic peptide

<400> SEQUENCE: 12

Ala Gly Tyr Leu Leu Gly Lys Ile Asn Leu Lys Ala Leu Ala Ala Leu
1               5                   10                  15

Ala Lys Lys Ile Leu
            20
```

POLYMER COMPOUND WHICH HAS MEMBRANE-PERMEABLE PEPTIDE IN SIDE CHAIN

TECHNICAL FIELD

The present invention relates to a polymer compound that is useful for introducing a poorly membrane-permeable compound into a cell or a mucous membrane.

BACKGROUND ART

In recent years, attempts have been made to elucidate functions of synthetic peptides, proteins, DNAs, and sugars or induce special functions by introducing these substances into a cell to adjust intracellular protein interaction and control intracellular signaling, transcription, or the like. With such an approach, it can be expected that genetic information that has been considered to be a mystery is elucidated, the causes of diseases are elucidated, and methods for treating the diseases are developed. Moreover, due to development of ES cells and iPS cells, a technique for controlling cell functions with nucleic acids or proteins becomes more important.

Water-soluble polymer substances such as polypeptides, nucleic acids, and sugars are usually highly hydrophilic, and thus have difficulty in passing through a cell membrane. Therefore, a microinjection method, an electroporation method, a calcium phosphate method, a lipofection method, a viral vector method, a membrane-permeable peptide method, and the like are known as a method for introducing these substances into a cell.

Of these methods, the membrane-permeable peptide method is a method that utilizes macropinocytosis of a cell induced by a membrane-permeable peptide. A method in which a target compound to be introduced into a cell and a membrane-permeable peptide are covalently bound and introduced (see Patent Literature 1 and 2, for example), and a method in which a polymer compound having a membrane-permeable peptide in a side chain and a target compound to be introduced into a cell are allowed to coexist and only the target compound is introduced (see Patent Literature 3 and 4, for example) are known as the membrane-permeable peptide method. With the method in which a target compound and a membrane-permeable peptide are covalently bound and introduced, cells are less damaged, but complex pretreatment is needed. On the other hand, the method using a polymer compound having a membrane-permeable peptide in a side chain is simple, but when a conventionally known polymer compound having a membrane-permeable peptide in a side chain is used, a water-soluble polymer substance is introduced with an insufficient efficiency, and a concentration at which the polymer compound is used is sometimes limited due to weak cytotoxicity of the polymer compound. Therefore, there is a problem with such a polymer compound when the efficiency of introducing the target compound is improved.

Also, the application of the polymer having a membrane-permeable peptide in a side chain to an agent for promoting the absorption of a medicine from the epithelium (see Patent Literature 5, for example) is proposed, but it is necessary to use the polymer at a high concentration in order to obtain a sufficient absorption promoting effect, and thus there is a concern about the irritation of a mucous membrane when the agent is put into practical use.

CITATION LIST

Patent Literature

Patent Literature 1: US 2003/229202A1
Patent Literature 2: JP 2005-052083A
Patent Literature 3: US 2010/113559A1
Patent Literature 4: JP 2011-229495A
Patent Literature 5: JP 2010-100781A

SUMMARY OF INVENTION

Technical Problem

The present invention was achieved in light of the aforementioned circumstances, and it is an object thereof to provide a polymer compound that allows a water-soluble polymer substance such as a nucleic acid or a protein or a medicine to be introduced into a cell or a mucous membrane with a high efficiency using a simple method, and an introduction method using the polymer compound.

Solution to Problem

The inventors of the present invention found that a polymer compound having a specific group having a membrane-permeable peptide in a side chain could be used to easily introduce a water-soluble polymer substance such as a nucleic acid or a protein or a medicine into a cell or a mucous membrane, and the present invention was thus achieved.

A polymer compound having a group represented by Formula (1) below or Formula (2) below in a side chain:

[Chem. 1]

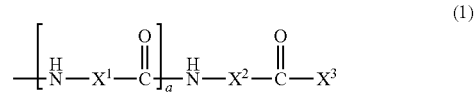

wherein $X^1$ represents a residue obtained by removing a terminal amino group and a terminal carboxyl group from a neutral amino acid or an ω-aminoalkanoic acid, $X^2$ represents a residue obtained by removing a terminal amino group and a terminal carboxyl group from a membrane-permeable peptide, $X^3$ represents a hydroxyl group, an amino group, an alkoxyl group having 1 to 4 carbon atoms, or a benzyloxy group, and a represents a number of from 1 to 50; and

[Chem. 2]

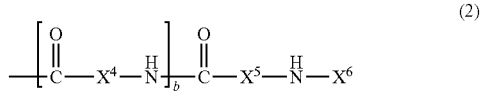

wherein $X^4$ represents a residue obtained by removing a terminal amino group and a terminal carboxyl group from a neutral amino acid or an ω-aminoalkanoic acid, $X^5$ represents a residue obtained by removing a terminal amino group and a terminal carboxyl group from a membrane-permeable peptide, $X^6$ represents a hydrogen atom, an alkyl group having 1 to 6 carbon atoms, a benzyl group, an acyl group having 1 to 6 carbon atoms, an arylsulfonyl group, or an oxycarbonyl group, and b represents a number of from 1 to 50.

The present invention provides an introducing agent for introducing a poorly membrane-permeable compound such as a medicine or a water-soluble polymer compound into a mucous membrane or a cell, the introducing agent being made of the above-mentioned polymer compound.

The present invention provides a method for introducing a poorly membrane-permeable compound into a cell or a mucous membrane that uses the above-mentioned introducing agent.

Advantageous Effects of Invention

With the present invention, a polymer compound having a group represented by Formula (1) or Formula (2) in a side chain can be used without undergoing complex pretreatment to introduce a poorly membrane-permeable compound into a cell or a mucous membrane with a high efficiency.

DESCRIPTION OF EMBODIMENTS

Hereinafter, an example of an embodiment of the present invention will be described, but the present invention is not limited to the following embodiment. It should be noted that a "poorly membrane-permeable compound" as used in the present invention means a compound having a low bioavailability, and specifically a compound having an extent of bioavailability of 50% or less. The extent of bioavailability can be calculated according to the following equation.

Extent of bioavailability (%)=100×(amount of orally administered substance that reaches blood)/ (amount of intravenously administered substance that reaches blood)

The "amount of substance that reaches blood" as used herein can be determined as an area of a portion surrounded by a blood level and a horizontal axis (time axis) (area under the drug blood level-time curve: AUC).

A polymer compound of the present invention and an introducing agent of the present invention that uses the polymer compound (the polymer compound and the introducing agent may also be collectively referred to as "polymer compound of the present invention" hereinafter) have a membrane-permeable peptide residue, and allow a poorly membrane-permeable compound to be efficiently taken up by a cell. In a mechanism in which a membrane-permeable peptide is taken up by a cell, generally, a membrane-permeable peptide induces macropinocytosis of a cell and is thus taken up, and it is thought that, when poorly membrane-permeable compounds are present around the membrane-permeable peptide, these poorly membrane-permeable compounds are taken up together with the membrane-permeable peptide. With the polymer compound of the present invention, macropinocytosis is induced at a plurality of positions of a cell by the membrane-permeable peptide residues, but the polymer compound of the present invention is a macromolecule, and a cell has a difficulty in taking up a single molecule of the polymer compound of the present invention at a plurality of positions. Therefore, when poorly membrane-permeable compounds are present around the polymer compound of the present invention, the poorly membrane-permeable compounds are accidentally and continuously taken up by the cell in which macropinocytosis is induced by the polymer compound of the present invention. Accordingly, it is thought that interaction between the membrane-permeable peptide residue and the poorly membrane-permeable compound is not necessarily required, and the poorly membrane-permeable compound can be introduced into a cell or a mucous membrane only by bringing a mixture of the polymer compound of the present invention and the poorly membrane-permeable compound into contact with a cell or a mucous membrane.

The polymer compound of the present invention is a graft-type polymer compound having a group represented by Formula (1) or Formula (2) in a side chain. In the present invention, the main chain portion of the polymer compound of the present invention is called a stem polymer. Hereinafter, the structure of the polymer compound of the present invention will be described in detail.

Group Represented by Formula (1)

In Formula (1), $X^1$ represents a residue obtained by removing the terminal amino group and the terminal carboxyl group from a neutral amino acid or an ω-aminoalkanoic acid, and a represents a number of from 1 to 50. Examples of the neutral amino acid include alanine, asparagine, cysteine, glutamine, glycine, isoleucine, leucine, methionine, phenylalanine, proline, serine, threonine, tryptophan, tyrosine, valine, and hydroxyproline, and examples of the ω-aminoalkanoic acid include 3-aminopropanoic acid, 4-aminobutanoic acid, 5-aminopentanoic acid, 6-aminohexanoic acid, 7-aminoheptanoic acid, 8-aminooctanoic acid, 9-aminononanoic acid, 10-aminodecanoic acid, and 11-aminoundecanoic acid. The neutral amino acid applied to $X^1$ is preferably glycine, alanine, valine, isoleucine, leucine, serine, threonine, or phenylalanine, more preferably glycine, alanine, or serine, and even more preferably glycine, because the efficiency of introducing a poorly membrane-permeable compound is improved, a is preferably a number of from 1 to 30, more preferably a number of from 1 to 20, and even more preferably a number of from 1 to 10. When a is a number of from 2 to 50, $X^1$ may be one of the neutral amino acid residues or the ω-aminoalkanoic acid residues, or a combination of two or more types selected from these residues.

In Formula (1), $X^2$ represents a residue obtained by removing the terminal amino group and the terminal carboxyl group from a membrane-permeable peptide. Although the membrane-permeable peptide residue of the polymer compound of the present invention may be selected as appropriate depending on a cell, a mucous membrane, or a poorly membrane-permeable compound to be introduced, it is preferable that at least one of the amino acids that constitute the membrane-permeable peptide residue is a basic amino acid. The basic amino acid may be an L-isomer or a D-isomer, and may be selected as appropriate depending on a cell, a mucous membrane, or a poorly membrane-permeable compound to be introduced.

Examples of the basic amino acid include arginine, ornithine, lysine, hydroxylysine, and histidine. Of these, an amino acid containing a guanidino group is preferable, and arginine is more preferable. The higher the ratio of the basic amino acids in the membrane-permeable peptide residue is, the more the efficiency of introducing a poorly membrane-permeable compound is improved, and therefore, the molar ratio of the basic amino acids with respect to the total amino acids that constitute the membrane-permeable peptide is preferably 50% or more, and more preferably 70% or more. It is preferable that, out of the amino acids that constitute the membrane-permeable peptide group, amino acids other than the basic amino acids are neutral amino acids. It should be noted that the term "amino acid" as mentioned herein refers to an α-amino acid unless otherwise stated.

The number of amino acids that constitute the membrane-permeable peptide group is preferably 5 to 30, more preferably 6 to 20, and even more preferably 7 to 15, because the efficiency of introducing a poorly membrane-permeable compound is improved.

Preferred specific examples of the membrane-permeable peptide include hydrophilic basic peptides such as an arginine oligomer obtained by binding 7 to 30 arginines via peptide bonds, a peptide having an amino acid sequence GRKKRRQRRRPPQ (known by the name HIV-1 Tat: Sequence ID No. 1), a peptide having an amino acid sequence TRQARRNRRRRWRERQR (known by the name HIV-1 Rev: Sequence ID No. 2), a peptide having an amino acid sequence RRRRNRTRRNRRRVR (known by the name FHV Coat: Sequence ID No. 3), a peptide having an amino acid sequence TRRQRTRRARRNR (known by the name HTLV-II Rex: Sequence ID No. 4), and a peptide having an amino acid sequence KLTRAQRRAAARKNKRNTR (known by the name CCMV Gag: Sequence ID No. 5); amphiphilic basic peptides such as a peptide having an amino acid sequence RQIKIWFQNRRMKWKK (known by the name Antennapedia: Sequence ID No. 6), a peptide having an amino acid sequence KMTRAQRRAAAR-RNRWTAR (known by the name BMW Gag: Sequence ID No. 7), a peptide having an amino acid sequence RQIKIW-FQNRRMKWKK (known by the name Penetratin: Sequence ID No. 8), a peptide having an amino acid sequence NAKTRRHERRRKLAIER (known by the name P22N: Sequence ID No. 9), and a peptide having an amino acid sequence DAATATRGRSAASRPTERPRAPARSASR-PDDPVD (known by the name VP22: Sequence ID No. 10); and hydrophobic basic peptides such as a peptide having an amino acid sequence GWTLNSAGYLLGKINLKA-LAALAKKIL (known by the name Transportan: Sequence ID No. 11) and a peptide having an amino acid sequence AGYLLGKINLKALAALAKKIL (known by the name TP-10: Sequence ID No. 12). Of these, the hydrophilic basic peptides are preferable, and the arginine oligomer is more preferable, because the efficiency of introducing a poorly membrane-permeable compound is excellent. The number of repeats of arginine in the arginine oligomer is preferably 7 to 20, more preferably 7 to 15, and even more preferably 7 to 10.

In Formula (1), $X^3$ represents a hydroxyl group, an amino group, an alkoxyl group having 1 to 4 carbon atoms, or a benzyloxy group. Examples of the alkoxyl group having 1 to 4 carbon atoms include a methoxy group, an ethoxy group, a propoxy group, an isopropoxy group, a butoxy group, an isobutoxy group, a 1-methylpropoxy group, and a t-butoxy group. $X^3$ is preferably a hydroxyl group, an amino group, a t-butoxy group, or a benzyloxy group, more preferably a hydroxyl group or an amino group, and even more preferably an amino group, from the viewpoint of the efficiency of introducing a poorly membrane-permeable compound.

When the polymer compound having a group represented by Formula (1) in a side chain has a plurality of groups represented by Formula (1), the groups represented by Formula (1) may have the same $X^1$, $X^2$, $X^3$, and a, or differ from one another in $X^1$, $X^2$, $X^3$, and a.

Group Represented by Formula (2)

In Formula (2), $X^4$ represents a residue obtained by removing the terminal amino group and the terminal carboxyl group from a neutral amino acid or an ω-aminoalkanoic acid, and b represents a number of from 1 to 50. Examples of the neutral amino acid include alanine, asparagine, cysteine, glutamine, glycine, isoleucine, leucine, methionine, phenylalanine, proline, serine, threonine, tryptophan, tyrosine, valine, and hydroxyproline, and examples of the ω-aminoalkanoic acid include 3-aminopropanoic acid, 4-aminobutanoic acid, 5-aminopentanoic acid, 6-aminohexanoic acid, 7-aminoheptanoic acid, 8-aminooctanoic acid, 9-aminononanoic acid, 10-aminodecanoic acid, and 11-aminoundecanoic acid. The neutral amino acid applied to $X^4$ is preferably glycine, alanine, valine, isoleucine, leucine, serine, threonine, or phenylalanine, more preferably glycine, alanine, or serine, and even more preferably glycine, from the viewpoint of the efficiency of introducing a poorly membrane-permeable compound and the viewpoint of the ease of synthesis. b is preferably a number of from 1 to 30, more preferably a number of from 1 to 20, and even more preferably a number of from 1 to 10. When b is a number of from 2 to 50, the neutral amino acid residues and the ω-aminoalkanoic acid residues may be used alone as $X^4$ or in combination of two or more.

In Formula (2), $X^5$ represents a residue obtained by removing the terminal amino group and the terminal carboxyl group from a membrane-permeable peptide. Although the membrane-permeable peptide residue of the polymer compound of the present invention may be selected as appropriate depending on a cell, a mucous membrane, or a poorly membrane-permeable compound to be introduced, it is preferable that at least one of the amino acids that constitute the membrane-permeable peptide residue is a basic amino acid. The basic amino acid may be an L-isomer or a D-isomer, and may be selected as appropriate depending on a cell, a mucous membrane, or a poorly membrane-permeable compound to be introduced.

Examples of the basic amino acid include arginine, ornithine, lysine, hydroxylysine, and histidine. Of these, an amino acid containing a guanidino group is preferable, and arginine is more preferable. The higher the ratio of the basic amino acids in the membrane-permeable peptide residue is, the more the efficiency of introducing a poorly membrane-permeable compound is improved, and therefore, the molar ratio of the basic amino acids with respect to the total amino acids that constitute the membrane-permeable peptide is preferably 50% or more, and more preferably 70% or more. It is preferable that, out of the amino acids that constitute the membrane-permeable peptide group, amino acids other than the basic amino acids are neutral amino acids.

The number of amino acids that constitute the membrane-permeable peptide group is preferably 5 to 30, more preferably 6 to 20, and even more preferably 7 to 15, because the efficiency of introducing a poorly membrane-permeable compound is improved.

Preferred specific examples of the membrane-permeable peptide include hydrophilic basic peptides such as an arginine oligomer obtained by binding 7 to 30 arginines via peptide bonds, a peptide having an amino acid sequence GRKKRRQRRRPPQ (known by the name HIV-1 Tat: Sequence ID No. 1), a peptide having an amino acid sequence TRQARRNRRRRWRERQR (known by the name HIV-1 Rev: Sequence ID No. 2), a peptide having an amino acid sequence RRRRNRTRRNRRRVR (known by the name FHV Coat: Sequence ID No. 3), a peptide having an amino acid sequence TRRQRTRRARRNR (known by the name HTLV-II Rex: Sequence ID No. 4), and a peptide having an amino acid sequence KLTRAQRRAAARKNKRNTR (known by the name CCMV Gag: Sequence ID No. 5); amphiphilic basic peptides such as a peptide having an amino acid sequence RQIKIWFQNRRMKWKK (known by the name Antennapedia: Sequence ID No. 6), a peptide having an amino acid sequence KMTRAQRRAAAR-RNRWTAR (known by the name BMW Gag: Sequence ID No. 7), a peptide having an amino acid sequence RQIKIW-FQNRRMKWKK (known by the name Penetratin: Sequence ID No. 8), a peptide having an amino acid sequence NAKTRRHERRRKLAIER (known by the name P22N: Sequence ID No. 9), and a peptide having an amino acid sequence DAATATRGRSAASRPTERPRAPARSASR-PDDPVD (known by the name VP22: Sequence ID No. 10); and hydrophobic basic peptides such as a peptide having an amino acid sequence GWTLNSAGYLLGKINLKA-LAALAKKIL (known by the name Transportan: Sequence ID No. 11) and a peptide having an amino acid sequence AGYLLGKINLKALAALAKKIL (known by the name TP-10: Sequence ID No. 12). Of these, the hydrophilic basic peptides are preferable, and the arginine oligomer is more preferable, because the efficiency of introducing a poorly membrane-permeable compound is excellent. The number of repeats of arginine in the arginine oligomer is preferably 7 to 20, more preferably 7 to 15, and even more preferably 7 to 10.

In Formula (2), $X^6$ represents a hydrogen atom, an alkyl group having 1 to 6 carbon atoms, a benzyl group, an acyl group having 1 to 6 carbon atoms, an arylsulfonyl group, or a carboxyl group. Examples of the alkyl group having 1 to 6 carbon atoms include a methyl group, an ethyl group, a propyl group, an isopropyl group, a butyl group, an isobutyl group, a secondary butyl group, a t-butyl group, a pentyl group, an isopentyl group, a secondary pentyl group, a t-pentyl group, a hexyl group, and a secondary hexyl group. Examples of the acyl group having 1 to 6 carbon atoms include a formyl group, an acetyl group, a propynoyl group, a butynoyl group, a pentynoyl group, and a hexynoyl group. Examples of the arylsulfonyl group include a p-toluenesulfonyl group, a 2-nitrobenzenesulfonyl group, and a trifluoroacetyl group. Examples of an oxycarbonyl group include a t-butoxycarbonyl group, a benzyloxycarbonyl group, 9-fluorenylmethyloxycarbonyl group, a 2,2,2-trichloroethoxycarbonyl group, and an allyloxycarbonyl group. $X^6$ is preferably an acetyl group, a hydrogen atom, a methyl group, or a trifluoroacetyl group, more preferably an acetyl group or a hydrogen atom, and even more preferably an acetyl group, from the viewpoint of the efficiency of introducing a poorly membrane-permeable compound.

When the polymer compound having a group represented by Formula (2) in a side chain has a plurality of groups represented by Formula (2), the groups represented by Formula (2) may have the same $X^4$, $X^5$, $X^6$, and b, or differ from one another in $X^4$, $X^5$, $X^6$, and b.

Stem Polymer Although there is no particular limitation on the stem polymer of the graft-type polymer of the present invention, a hydrophilic polymer has an excellent affinity for a cell and a water-soluble polymer substance such as a protein, and thus is preferable as the stem polymer. Here, the "hydrophilic polymer" means a water-soluble polymer or a polymer that swells in water. The "water-soluble polymer" as used in the present invention refers to a polymer that uniformly dissolves in an amount of 0.1 mass % or more in water at 25° C. under normal pressures.

Examples of the hydrophilic polymer include polysaccharides such as guar gum, agarose, mannan, glucomannan, polydextrose, lignin, chitin, chitosan, carageenan, pullulan, chondroitin sulfate, cellulose, hemicellulose, methylcellulose, ethylcellulose, hydroxyethylcellulose, hydroxypropylcellulose, starch, cationic starch, and dextrin or modified polysaccharides; water-soluble proteins or water-soluble polypeptides such as albumin, casein, gelatin, polyglutamic acid, and polylysine; vinyl-based hydrophilic polymer such as poly(meth)acrylic acid, poly(hydroxyethyl acrylate), poly (meth)acrylamide, poly N-vinylacetamide, polyvinylpyrrolidone, polyvinyl alcohol, poly(2-aminoethyl(meth)acrylate), a (meth)acrylic acid-acrylamide copolymer, a (meth) acrylic acid-N-isopropylacrylamide copolymer, a (meth) acrylic acid-N-vinylacetamide copolymer, (meth)acrylic acid-maleic acid copolymer, (meth)acrylic acid-fumaric acid copolymer, ethylene-maleic acid copolymer, isobutylene/maleic acid copolymer, styrene/maleic acid copolymer, alkyl vinyl ether-maleic acid copolymer, and alkyl vinyl ether-fumaric acid copolymer; and water-soluble polyurethane When the polymer compound having a group represented by Formula (1) in a side chain is used as the polymer compound of the present invention, the stem polymer is preferably a polymer having a carboxyl group, more preferably a hydrophilic polymer having a carboxyl group, even more preferably a copolymer of a monomer having a carboxyl group and a monomer having no carboxyl group, and even more preferably a (meth)acrylic acid-N-vinylacetamide copolymer, because grafting of the membrane-permeable peptide groups to the stem polymer is facilitated.

When the polymer compound having a group represented by Formula (2) in a side chain is used, the stem polymer is preferably a polymer having an amino group, more preferably a hydrophilic polymer having an amino group, and even more preferably chitosan. It should be noted that "having an amino group or a carboxyl group" could be applied to the stem polymer in which a group represented by Formula (1) or (2) had not been yet provided in a side chain.

When the stem polymer has a carboxyl group, the ratio of the number of monomer units having a carboxyl group with respect to the number of monomer units that constitute the stem polymer is preferably 5 to 80%, and more preferably 10 to 60%, from the viewpoint of easily forming a polymer compound that can be favorably used as the polymer compound of the present invention, for example.

When the stem polymer has an amino group, the ratio of the number of monomer units having an amino group with respect to the number of monomer units that constitute the stem polymer is preferably 5 to 100%, and more preferably 10 to 100%, from the viewpoint of easily forming a polymer compound that can be favorably used as the polymer compound of the present invention, for example. It is preferable that the ratio of the number of units having an amino group or a carboxyl group as described above is applied to the stem polymer in which a group represented by Formula (1) or (2) has not been yet provided in a side chain.

Polymer Compound of the Present Invention

The polymer compound of the present invention is characterized by having a group represented by Formula (1) or Formula (2) in a side chain. When the ratio of the groups represented by Formula (1) or Formula (2) in the polymer compound of the present invention is too low or too high, the efficiency of introducing a poorly membrane-permeable compound decreases, and therefore, the ratio of the number of groups represented by Formula (1) or Formula (2) in the polymer compound of the present invention with respect to the number of monomer units (monosaccharide units in a case of a polysacchride or a modified polysaccharide, and amino acid units in a case of a water-soluble protein or a water-soluble polypeptide) that constitute the stem polymer is preferably 0.001 to 0.9, more preferably 0.005 to 0.8, and even more preferably 0.01 to 0.7.

When the size of the polymer compound of the present invention is too small, the polymer compound of the present invention is likely to be taken up by a cell, and when the size of the polymer compound of the present invention is too large, the efficiency of introducing a poorly membrane-permeable compound to be introduced decreases. Therefore, the polymer compound of the present invention has a weight-average molecular weight of preferably 100,000 to 50,000,000, more preferably 200,000 to 30,000,000, and even more preferably 300,000 to 10,000,000. It should be noted that the "weight-average molecular weight" as used in the present invention refers to a weight-average molecular weight obtained through GPC analysis using an aqueous solvent, and to a weight-average molecular weight in terms of pullulan in a case where a polysaccharide, a modified polysaccharide, or a water-soluble protein is used as the stem polymer, and to a weight-average molecular weight in terms of polyethylene glycol (PEG) or polyethylene oxide (PEO) in a case where a vinyl-based hydrophilic polymer is used as the stem polymer.

The poorly membrane-permeable compound is introduced with a higher efficiency in a case where the polymer compound of the present invention is used than a case where a conventionally known polymer compound having a membrane-permeable peptide in a side chain is used. It is inferred that the reason for this is that, while a membrane-permeable peptide is directly bound to the stem polymer in a conventionally known polymer compound having a membrane-permeable peptide in a side chain (see JP 2010-100781A, for example), a membrane-permeable peptide is bound to the stem polymer via a group represented by Formula (1a) below or Formula (2a) below in the polymer compound of the present invention, and thus the degree of freedom of the membrane-permeable peptide residue is improved. Moreover, there is the advantage that, due to interposition of a group represented by Formula (1a) below or Formula (2a) below, substitution of the stem polymer with a group having a membrane-permeable peptide can be performed in a milder condition at a higher substitution ratio in the polymer compound of the present invention than in a conventionally known polymer compound having a membrane-permeable peptide in a side chain

[Chem. 3]

(1a)

(In the formula, $X^1$ and a are the same as those defined in Formula (1).)

[Chem. 4]

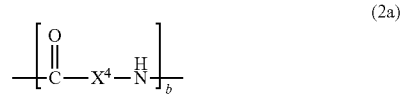
(2a)

(In the formula, $X^4$ and b are the same as those defined in Formula (2).)

Method for Manufacturing Polymer Compound of the Present Invention

There is no particular limitation on a method for manufacturing the polymer compound of the present invention, and the polymer compound of the present invention may be manufactured through the polymerization of polymerizable monomers having a group represented by Formula (1) or Formula (2) or through the introduction of a group represented by Formula (1) or Formula (2) into the stem polymer, but it is preferable that the polymer compound of the present invention is manufactured through the introduction of a group represented by Formula (1) or Formula (2) into the stem polymer from the viewpoint of the ease of manufacturing. When a hydrophilic polymer having a carboxyl group is used as the stem polymer, the polymer compound of the present invention can be obtained through a peptide reaction between the carboxyl group and the amino group of a peptide compound represented by Formula (1b) below. It is sufficient that the reaction between the carboxyl group and the amino group is performed using a known method, and an example thereof is a method in which a carboxyl group is made into a succinimide ester using N-hydroxysuccinimide, followed by the reaction with an amino group. When a hydrophilic polymer having an amino group is used as the stem polymer, the polymer compound of the present invention can be obtained through a peptide reaction between the amino group and the carboxyl group of a peptide compound represented by Formula (2b) below. With this method, a group represented by Formula (1) or (2) can be most easily introduced as a side chain of the stem polymer via an amide bond. However, a method for immobilizing a group represented by Formula (1) or (2) is not limited to this method, and generally known chemical reaction can be used to immobilize the aforementioned group.

[Chem. 5]

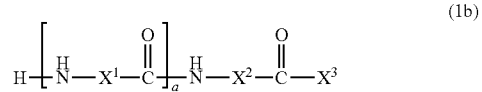
(1b)

(In the formula, $X^1$, $X^2$, $X^3$, and a are the same as those defined in Formula (1).)

[Chem. 6]

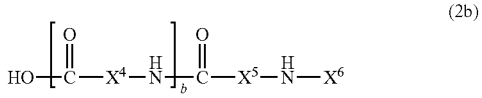
(2b)

(In the formula, $X^4$, $X^5$, $X^6$, and b are the same as those defined in Formula (2).)

Poorly Membrane-Permeable Compound

The polymer compound of the present invention can be used as an introducing agent for introducing a poorly membrane-permeable compound into a cell or a mucous membrane to introduce various poorly membrane-permeable compounds. Examples of the poorly membrane-permeable compounds include: drugs such as a peptide/protein drug including insulin, an insulin secretion promoter (e.g., exendin-4 and GLP-1), or the like, a steroid hormone, a non-steroidal analgesic anti-inflammatory drug, a tranquilizer, an anti-hypertensive drug, a therapeutic drug for an ischemic heart disease, an anti-histamine drug, an anti-asthmatic drug, an anti-Parkinson drug, a cerebral circulation improving drug, an anti-emetic drug, an anti-depressant drug, an anti-arrhythmic drug, an anti-coagulant drug, an anti-gout drug, an anti-fungal drug, an anti-dementia drug, a therapeutic drug for Sjögren's syndrome, a narcotic analgesic drug, a beta blocker, a β1 agonist, a β2 agonist, a parasympathomimetic drug, an anti-tumor drug, a diuretic drug, an anti-thrombotic drug, a histamine H1 receptor antagonist, a histamine H2 receptor antagonist, an anti-allergic drug, a smoking cessation drug, and a vitamin;

nucleic acid compounds such as a deoxyribonucleic acid (DNA), a ribonucleic acid (RNA), and analogs or derivatives thereof (e.g., a peptide nucleic acid (PNA) and a phosphorothioate DNA); peptide compounds such as an enzyme, an antibody, a glycoprotein, and a transcription factor; and polysaccharide derivatives such as pullulan, amylopectin, amylose, glycogen, cyclodextrin, dextran, hydroxyethyldextran, mannan, cellulose, starch, alginic acid, chitin, chitosan, and hyaluronic acid, and derivatives thereof.

Although any of animal cells, plant cells, bacteria, and the like may be used as cells to which the polymer compound of the present invention is applied, it is preferable to use cells of mammals such as the human from the viewpoint of the efficiency of introducing a poorly membrane-permeable compound. It is also preferable to use cells of mammals such as the human as a mucous membrane to which the polymer compound of the present invention is applied from the viewpoint of the efficiency of introducing a poorly membrane-permeable compound.

Cell

The polymer compound of the present invention can be used to introduce a poorly membrane-permeable compound into various types of cells, and thus the poorly membrane-permeable compound can be introduced into any of cells such as cells that are dispersed in a culture solution (also referred to as "liquid culture medium") or the like, cells that adhere to a solid culture medium or the like, and cells of a body tissue. Cells can be broadly divided into adherent cells that include tissue cells, nerve cells, and the like, and floating cells such as hemocytes. A microinjection method or an electroporation method cannot be applied to floating cells, and a calcium phosphate method, a lipofection method, a viral vector method, or the like can be applied thereto, but the introduction efficiency is not satisfying. With the introduction method of the present invention, the poorly membrane-permeable compound can be introduced into not only adherent cells but also floating cells with a high introduction efficiency.

Method of Introduction into Cell

When the polymer compound of the present invention is used to introduce the poorly membrane-permeable compound into a cell, it is sufficient that an aqueous solution or an aqueous dispersion containing the polymer compound of the present invention and the poorly membrane-permeable compound is brought into contact with the cell. Therefore, such complex pretreatment that is required in a viral vector method or in a conventional introduction method using a membrane-permeable peptide is not required, and the poorly membrane-permeable compound can be introduced into the cell without a great adverse influence on the cell.

Although examples of an aqueous medium in which the polymer compound of the present invention and the poorly membrane-permeable compound are dissolved or dispersed to form an aqueous solution or an aqueous dispersion containing these compounds include distilled water and a culture solution to be generally used for cell culture as well as isotonic water such as a physiological saline solution and a 5 mass % aqueous solution of glucose, the culture solution, the physiological saline solution, and the 5 mass % aqueous solution of glucose have little influence on cells and are thus preferable.

When cells are suspended in an aqueous solution or an aqueous dispersion, it is sufficient that the cells are suspended in the aqueous solution or the aqueous dispersion containing the poorly membrane-permeable compound and the polymer compound of the present invention, and the suspension containing the cells, the poorly membrane-permeable compound, and the polymer compound may be stirred or shaken as needed. When cells cannot be suspended in an aqueous solution or an aqueous dispersion for the reason that the cells adhere to a solid culture medium or a cellular tissue has a large size, it is sufficient that the cells are immersed in the aqueous solution or the aqueous dispersion containing the poorly membrane-permeable compound and the polymer compound of the present invention.

When the poorly membrane-permeable compound is introduced into a cell, there is no particular limitation on the use concentration of the polymer compound of the present invention, but it is preferable to set the use concentration to 0.1 µg/mL to 10 mg/mL in the aqueous solution or the aqueous dispersion. In addition, there is no particular limitation on the concentration of the poorly membrane-permeable compound to be introduced, but it is preferable to set the concentration to 0.5 µg/mL to 10 mg/mL in the aqueous solution or the aqueous dispersion. Furthermore, there is no limitation on the concentration of cells when the cells are suspended in a culture solution or a physiological saline solution, but it is preferable to set the concentration to 10,000 to 2,000,000 cells/mL in the aqueous solution or the aqueous dispersion.

Although there is no limitation on a period of time when the polymer compound of the present invention, the poorly membrane-permeable compound to be introduced, and the cells are allowed to coexist, it is preferable to set the period of time to 30 minutes to 24 hours.

Mucous Membrane

The polymer compound of the present invention can be used in a mucous membrane to introduce the poorly membrane-permeable compound into various types of mucous membranes. Examples of the mucous membrane include the nasal mucous membrane, the oral mucous membrane, the vaginal mucous membrane, the rectal mucous membrane, the ocular mucous membrane, the gastric mucous membrane, and the intestinal mucous membrane. A conventional polymer compound having a membrane-permeable peptide in a side chain has a high mucous membrane irritating property and thus causes an itch in some cases when used in the nasal mucous membrane, for example, but with the polymer compound of the present invention, such an itch is reduced.

Method of Introduction into Mucous Membrane

When the polymer compound of the present invention is used to introduce the poorly membrane-permeable compound into a mucous membrane, it is sufficient that a mixture of the polymer compound of the present invention and the poorly membrane-permeable compound is brought into close contact with the mucous membrane, and there is no limitation on a dosage form as long as the mixture has a dosage form that makes it less likely that the mixture separates from the mucous membrane. Although a preferred dosage form varies depending on the type of mucous membrane, examples thereof include a pill, a tablet, a troche, a patch, a suppository, and a poultice. It is sufficient that the form of a mixture with the mixture of the polymer compound of the present invention and the poorly membrane-permeable compound is selected from forms such as a liquid form, an emulsion form, a suspension form, a gel form, a powder form, and a solid form depending on the dosage form. One type of the poorly membrane-permeable compounds may be introduced or a combination of two or more types of the poorly membrane-permeable compounds may be introduced according to the purpose. In addition, a vehicle, an emulsifier, a dispersant, a gelling agent, a humectant, or the like may be used in addition as needed.

Use of Microprojection Array

The polymer compound of the present invention cannot be used to introduce the poorly membrane-permeable compound into a cell through the skin, but a microprojection array (a medicine delivery member obtained by arranging minute projections on a sheet; see US 2005025778A1, JP 2008-006178A, and the like, for example) can be used to introduce the poorly membrane-permeable compound into a cell under the skin. For example, the poorly membrane-permeable compound can be introduced into a cell under the skin by attaching, on the skin surface, a microprojection array in which the mixture of the polymer compound of the present invention and the poorly membrane-permeable compound is applied to the surface or a microprojection array having microprojections including the mixture of the polymer compound of the present invention and the poorly membrane-permeable compound, passing the minute projections through the skin, and infiltrating the polymer compound of the present invention and the poorly membrane-permeable compound under the skin.

EXAMPLES

Hereinafter, the present invention will be further described by way of examples, but the present invention is not limited to these examples. It should be noted that, unless otherwise stated, "part" and "%" as used in the examples refer to "part by mass" and "mass %", respectively.

Example 1

10 g of an N-vinylacetamide-sodium acrylate copolymer (product name: GE160-105; manufactured by Showa Denko K.K.) was dissolved in 1 kg of ion-exchanged water, and 10 g of a strongly acidic cation exchange resin (product name: Amberlyst 15 DRY; manufactured by Organo Corporation) was added to the solution. After the resulting mixture was stirred for 2 hours, the ion exchange resin was filtered out. The filtrate was concentrated and lyophilized, and thus 8.6 g of an N-vinylacetamide-acrylate copolymer (referred to as "GE160-105H" hereinafter) was obtained.

500 mg of GE160-105H was dissolved in 15 mL of dimethylformamide (DMF). This solution was cooled to 0° C., 1.1 g of N-hydroxysuccinimide dissolved in 5 mL of DMF was added thereto, and then 1.96 g of dicyclohexylcarbodiimide (DCC) dissolved in 5 mL of DMF was further added. The resulting solution was stirred at room temperature (25° C.) for 24 hours and reacted. A solid precipitate was filtered out by filtration, the filtrate was slowly dripped in 500 mL of acetonitrile to perform reprecipitation, and thus 620 mg of a succinimide ester of GE160-105 (referred to as "GE160-105OSu" hereinafter) was obtained.

20 mg of GE160-105OSu was dissolved in 0.2 mL of DMF, and 148 mg of a compound (manufactured by RS Synthesis; product name: H-(Gly)4-(D-Arg)8-NH2 (Purity: 90%), TFA Salt) represented by Formula (1b) in which a was 4, $X^1$ was a residue obtained by removing the terminal amino group and the terminal carboxyl group from glycine, $X^2$ was a residue obtained by removing the terminal amino group and the terminal carboxyl group from octaarginine, and $X^3$ was an amino group was dissolved in 0.8 mL of DMF and mixed thereinto. The resulting solution was stirred at 60° C. for 24 hours and reacted. After the reaction, the reaction solution was poured in a cellulose dialysis tube (seamless cellulose tube; manufactured by Wako Pure Chemical Industries, Ltd.), and the solution in the tube whose both ends were tied up was dialyzed using ion-exchanged water for 2 days. Thereafter, the content of the tube was lyophilized, and thus 62 mg of a polymer compound of Example 1 was obtained. The polymer compound of Example 1 was a compound represented by Formula (1) in which $X^1$ was a residue obtained by removing the terminal amino group and the terminal carboxyl group from glycine, $X^2$ was a residue obtained by removing the terminal amino group and the terminal carboxyl group from octaarginine, $X^3$ was an amino group, and a was 4. The polymer compound of Example 1 had a weight-average molecular weight of 1,600,000, and it was found from the integral values obtained by NMR that the polymer compound had the following structure. It should be noted that, in this formula, Gly represents a glycine residue, Arg represents an arginine residue, and x:y:z=70:1:29.

[Chem. 7]

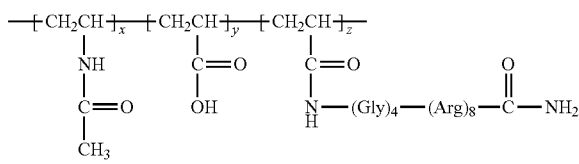

Example 2

54 mg of a polymer compound of Example 2 was obtained by conducting the operations in the same manner as in Example 1, except that the use amount of H-(Gly)4-(D-Arg)8-NH2 was changed from 148 mg to 50 mg. The polymer compound of Example 2 was a compound represented by Formula (1) in which $X^1$ was a residue obtained by removing the terminal amino group and the terminal carboxyl group from glycine, $X^2$ was a residue obtained by removing the terminal amino group and the terminal carboxyl group from octaarginine, $X^3$ was an amino group, and a was 4. The polymer compound of Example 2 had a weight-average molecular weight of 1,600,000, and it was found from the integral values obtained by NMR that the polymer compound had the following structure. It should be noted that, in this formula, Gly represents a glycine residue, Arg represents an arginine residue, and x:y:z=70:15:15.

[Chem. 8]

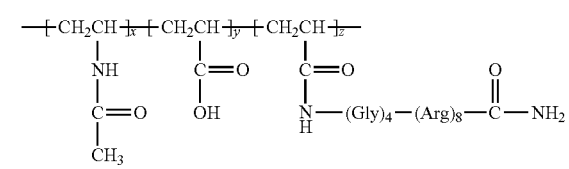

Example 3

150 mg of a compound (manufactured by RS Synthesis; product name: HO-(Gly)4-(D-Arg)8-COCH3 (Purity: 90%)) represented by Formula (2b) in which b was 4, $X^4$ was a residue obtained by removing the terminal amino group and the terminal carboxyl group from glycine, $X^5$ was a residue obtained by removing the terminal amino group and the terminal carboxyl group from octaarginine, and $X^6$ was an acetyl group was dissolved in 0.5 mL of DME After 132 mg of N-hydroxysuccinimide was added thereto, 230 mg of DCC dissolved in 0.3 mL of DMF was added. Furthermore, a solution (100 mg/mL) of chitosan having a weight-average molecular weight of about 100,000 in DMF was added, and the resulting solution was stirred at room temperature (25° C.) for 24 hours. The reaction solution was poured in a cellulose dialysis tube (seamless cellulose tube; manufactured by Wako Pure Chemical Industries, Ltd.), and the solution in the tube whose both ends were tied up was dialyzed using ion-exchanged water for 2 days. Thereafter, the content of the tube was lyophilized, and thus 32 mg of a polymer compound of Example 3 was obtained. The polymer compound of Example 3 had a weight-average molecular weight of 110,000, and it was found from the integral values obtained by NMR that the polymer compound had the following structure. It should be noted that, in this formula, Gly represents a glycine residue, Arg represents an arginine residue, and x:y=80:20.

manufacturing example in US 2010113559A1. The polymer compound of Comparative Example 2 was a compound having the following structure. It should be noted that, in this formula, Arg represents an arginine residue, and x:y=80:20.

[Chem. 11]

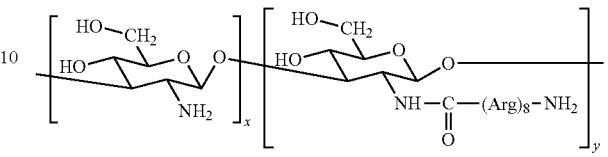

Cell

CHO cells: cells derived from the ovaries of Chinese hamsters

Culture Medium

Ham's F12 culture medium (product name; manufactured by Wako)

[Chem. 9]

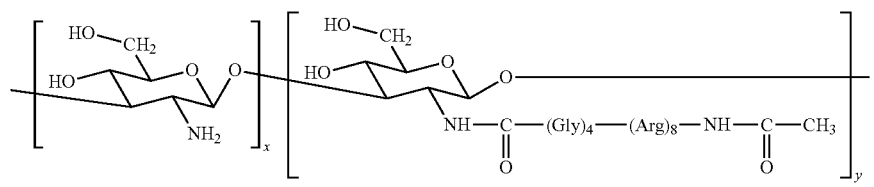

Comparative Example 1

32 mg of a polymer compound of Comparative Example 1 was obtained by conducting the operations in the same manner as in Example 1, except that 0.5 mL of a solution (350 mg/mL) of a compound (manufactured by GL Biochem; product name: RRRRRRRR—NH2, [R=D-Arg] TFA Salt) obtained by amidating the terminal carboxyl group of octaarginine in DMSO was used instead of the solution of H-(Gly)4-(D-Arg)8-NH2 in DMF. The polymer compound of Comparative Example 1 had a weight-average molecular weight of 1,600,000, and it was found from the integral values obtained by NMR that the polymer compound had the following structure. It should be noted that, in this formula, Arg represents an arginine residue, and x:y:z=70:15:15.

[Chem. 10]

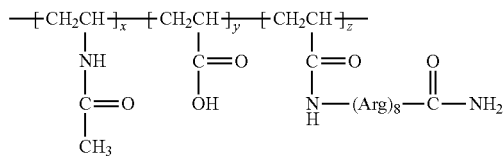

Comparative Example 2

A polymer compound of Comparative Example 2 was manufactured using chitosan having a weight-average molecular weight of about 100,000 in accordance with the Opti-MEM culture medium (product name; manufactured by Life Technologies) Agent Trypsin-EDTA solution: aqueous solution of 0.25% trypsin and 1 mmol/L EDTA Poorly Membrane-Permeable Compound FITC-BSA: Fluorescein-labeled bovine serum albumin (manufactured by Sigma-Aldrich)

Efficiency of Introduction into Cell

500 µL of a suspension ($2 \times 10^5$ cells/mL) of CHO cells in a Ham's F12 culture medium was seeded in each well of a 24-well plate, and preculture was performed in a carbon dioxide incubator for 24 hours. After the supernatant culture medium was removed, 250 µL of a solution (10 µg/mL) of FITC-BSA in an Opti-MEM culture medium was added. Furthermore, 250 µL of a solution (100 µg/mL) of each of the polymer compounds of Examples 1 to 3 and Comparative Examples 1 and 2 in an Opti-MEM culture medium was added, and the cells were cultured in a carbon dioxide incubator for 1 hour. The supernatant culture medium solution was removed, and the cells were washed twice using 500 µL of a phosphate-buffered physiological saline solution. Thereafter, 100 µL of a trypsin-EDTA solution was added, and thus the cultured CHO cells were separated from the plate and dispersed. Next, 100 µL of a 0.08% solution of trypan blue was added, and the cells were suspended and then collected in a microtube. The collected cell suspension was passed through a cell strainer, and MFI (mean fluorescence intensity) was measured using flow cytometry. A sample in which no polymer compound was used was taken as a blank. Table 1 shows the results.

TABLE 1

| | MFI |
|---|---|
| Ex. 1 | 181 |
| Ex. 2 | 157 |
| Ex. 3 | 129 |
| Comp. Ex. 1 | 127 |
| Comp. Ex. 2 | 42.4 |
| Blank | 5.64 |

Extracellular FITC-BSA is deactivated by trypan blue and thus emits no fluorescence, and only FITC-BSA that has introduced into a cell emits fluorescence. MFI refers to a mean value of fluorescence intensity per cell, and therefore, a larger MFI value means that FITC-BSA, which is a water-soluble polymer compound, is taken up by a cell in a larger amount. It is found from the results shown in Table 1 that, when the polymer compounds of Examples 1 to 3 were used, the water-soluble polymer substance was introduced into a cell with a high efficiency.

The invention claimed is:

1. A polymer compound having a group represented by Formula (1) below or Formula (2) below in a side chain:

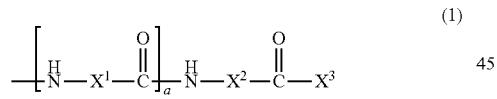

wherein $X^1$ represents a residue obtained by removing a terminal amino group and a terminal carboxyl group from glycine, $X^2$ represents a residue obtained by removing a terminal amino group and a terminal carboxyl group from octaarginine, $X^3$ represents a hydroxyl group, an amino group, an alkoxyl group having 1 to 4 carbon atoms, or a benzyloxy group, and "a" is 4; and

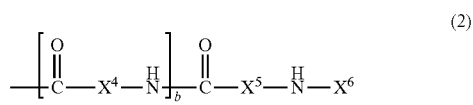

wherein $X^4$ represents a residue obtained by removing a terminal amino group and a terminal carboxyl group from glycine, $X^5$ represents a residue obtained by removing a terminal amino group and a terminal carboxyl group from octaarginine, $X^6$ represents a hydrogen atom, an alkyl group having 1 to 6 carbon atoms, a benzyl group, an acyl group having 1 to 6 carbon atoms, an arylsulfonyl group, or an oxycarbonyl group, and "b" is 4;

said polymer compound comprising acrylic acid-N-vinylacetamide copolymer as a stem polymer.

2. An introducing agent for introducing a poorly membrane-permeable compound into a cell or a mucous membrane, the introducing agent comprising the polymer compound according to claim 1.

3. A method for introducing a poorly membrane-permeable compound into a cell, the method comprising administering the introducing agent according to claim 2 into a cell.

4. A method for introducing a poorly membrane-permeable compound into a mucous membrane, the method comprising administering the introducing agent according to claim 2 into a mucous membrane.

* * * * *